(12) United States Patent
Jevsevar et al.

(10) Patent No.: US 7,655,437 B2
(45) Date of Patent: Feb. 2, 2010

(54) **SYNTHETIC GENE CODING FOR HUMAN GRANULOCYTE-COLONY STIMULATING FACTOR FOR THE EXPRESSION IN *E. COLI***

(75) Inventors: Simona Jevsevar, Maribor (SI); Viktor Menart, Logatec (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 522 days.

(21) Appl. No.: 10/522,827

(22) PCT Filed: Jul. 28, 2003

(86) PCT No.: PCT/EP03/08308

§ 371 (c)(1), (2), (4) Date: Jan. 31, 2005

(87) PCT Pub. No.: WO2004/013175

PCT Pub. Date: Feb. 12, 2004

(65) Prior Publication Data

US 2006/0228781 A1 Oct. 12, 2006

(30) Foreign Application Priority Data

Jul. 31, 2002 (SI) .............................. P-200200188

(51) Int. Cl.
*C12N 15/00* (2006.01)
*C12N 15/11* (2006.01)
*C07K 14/00* (2006.01)

(52) U.S. Cl. .................... 435/69.1; 435/69.5; 536/23.1; 530/350

(58) Field of Classification Search ....................... None
See application file for complete search history.

(56) References Cited

U.S. PATENT DOCUMENTS 5,840,543 A * 11/1998 Hockney et al. ........... 435/69.5

OTHER PUBLICATIONS

Baneyx et al., Curr. Opin. Biotech., 1999, 10:411-421.*
Krishna Rao et al., Mol. Biotechnol., 2008, 38(3):221-32.*
Devlin et al., Alteration of amino-terminal codons of human granulocyte-colony-stimulating factor increases expression levels and allows efficient processing by methionine aminopeptidase in *Escherichia coli*, Gene, 1988, p. 13-22, vol. 65, Elsevier Science Publishers B.V., USA.
Kane, Effects of rare codon clusters on high-level expression of heterologous proteins in *Escherichia coli*, Current Opinion in Biotechnology, 1995, p. 494-500, vol. 6, Current Biology Ltd., USA.
Jeong et al., Secretory Production of Human Granulocyte Colony-Stimulating Factor in *Escherichia coli*, Protein Expression and Purification, 2001, p. 311-318, vol. 23, Academic Press, USA.
Makrides, Strategies for achieving high-level expression of genes in *Escherichia coli*, Microbiological Reviews, Sep. 1996, p. 512-538, American Society for Microbiology, USA.

* cited by examiner

*Primary Examiner*—Gary B Nickol
*Assistant Examiner*—Xiaozhen Xie
(74) *Attorney, Agent, or Firm*—Luedeka, Neely & Graham, P.C.

(57) ABSTRACT

The invention relates to the synthetic gene coding for hG-CSF which enables expression in *E. coli* with an improved expression level of the recombinant hG-CSF regarding the total cellular proteins after expression.

13 Claims, 5 Drawing Sheets

Figure 2 a)

ATGACCCCCCTGGGCCCTGCCAGCTCCCTGCCCCAGAGCTTCCTGCTCAAGTG
CTTAGAGCAAGTGAGGAAGATCCAGGGCGATGGCGCAGCGCTCCAGGAGAAGC
TGTGTGCCACCTACAAGCTGTGCCACCCCGAGGAGCTGGTGCTGCTCGGACAC
TCTCTGGGCATCCCCTGGGCTCCCCTGAGCTCCTGCCCCAGCCAGGCCCTGCA
GCTGGCAGGCTGCTTGAGCCAACTCCATAGCGGCCTTTTCCTCTACCAGGGGC
TCCTGCAGGCCCTGGAAGGGATATCCCCCGAGTTGGGTCCCACCTTGGACACA
CTGCAGCTGGACGTCGCCGACTTTGCCACCACCATCTGGCAGCAGATGGAAGA
ACTGGGAATGGCCCCTGCCCTGCAGCCCACCCAGGGTGCCATGCCGGCCTTCG
CCTCTGCTTTCCAGCGCCGGGCAGGAGGGGTCCTGGTTGCTAGCCATCTGCAG
AGCTTCCTGGAGGTGTCGTACCGCGTTCTACGCCACCTTGCGCAGCCC b)

ATGACACCACTGGGTCCAGCTTCTTCTCTGCCGCAAAGCTTTCTGTTGAAATG
TTTAGAACAAGTTCGTAAAATTCAAGGTGATGGTGCAGCTTTACAAGAAAAAC
TGTGTGCAACTTATAAACTGTGTCATCCAGAAGAACTGGTTCTGTTAGGTCAT
TCTCTGGGTATTCCGTGGGCTCCTCTGAGCTCCTGTCCGAGCCAGGCGCTGCA
GCTGGCAGGCTGCCTGAGCCAACTGCATAGCGGTCTGTTTCTGTATCAGGGTC
TGCTGCAGGCGCTGGAAGGCATTTCCCCGGAACTGGGGCCCACCTTGGACACA
CTGCAGCTGGACGTCGCCGACTTTGCCACCACCATCTGGCAGCAGATGGAAGA
ACTGGGAATGGCCCCTGCCCTGCAGCCCACCCAGGGTGCCATGCCGGCCTTCG
CCTCTGCTTTCCAGCGCCGTGCAGGTGGGGTCCTGGTTGCTAGCCATCTGCAA
TCTTTTCTGGAAGTTAGCTATCGTGTTCTGCGTCATCTGGCTCAGCCG

Figure 3
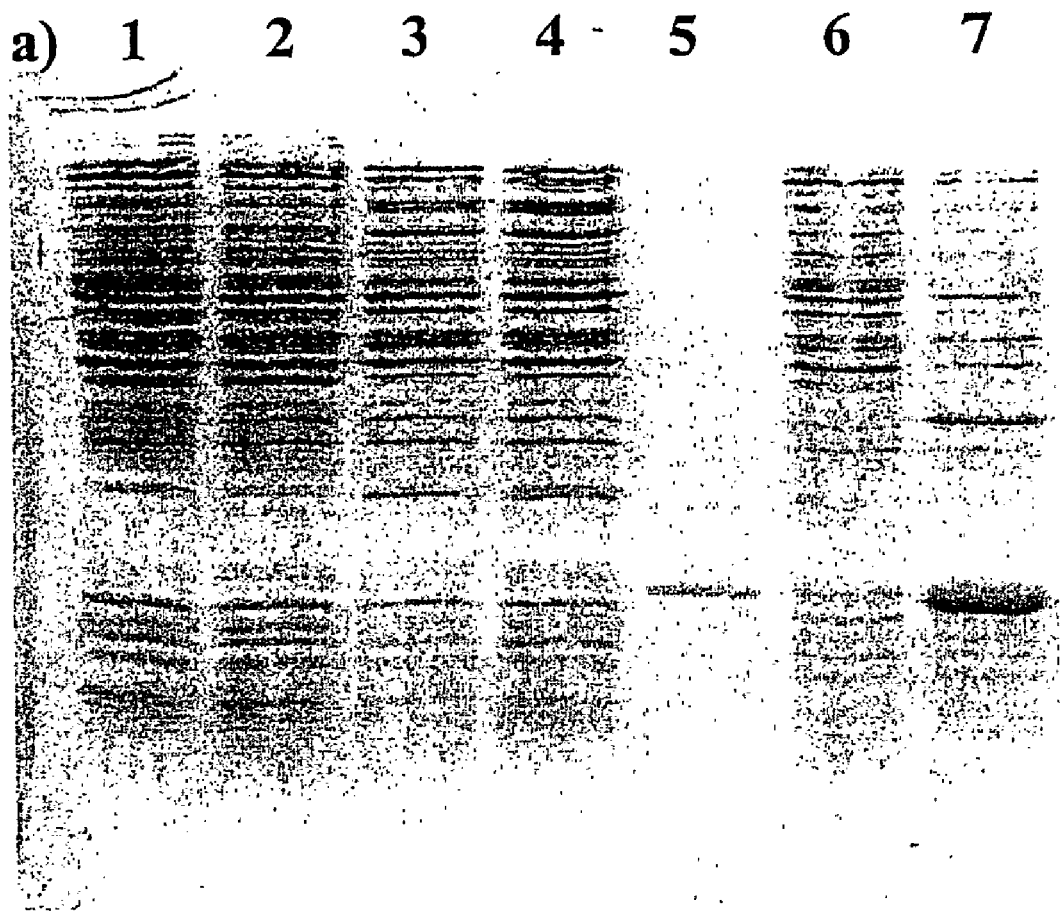

SYNTHETIC GENE CODING FOR HUMAN GRANULOCYTE-COLONY STIMULATING FACTOR FOR THE EXPRESSION IN E. COLI

FIELD OF THE INVENTION

The present invention relates to a synthetic gene coding for human granulocyte-colony stimulating factor (hG-CSF) which enables expression in E. coli with an improved expression level, enabling an expression level equal to or higher than 52% of the recombinant hG-CSF to the total proteins after expression.

hG-CSF belongs to a family of stimulating factors which regulate the differentiation and proliferations of hematopoetic mammalian cells. They have a major role in neutrophil formation and are therefore suitable for use in medicine in the field of hematology and oncology.

Two forms of hG-CSF are currently available for clinical use on the market: lenograstim which is glycosylated and is obtained by the expression in mammalian cell line; and filgrastim, which is non-glycosylated and is obtained by the expression in the bacterium Escherichia coli (E. coli).

BACKGROUND OF THE INVENTION

The impact of several successive rare codons such as arginine codons (AGG/AGA; CGA), leucine codon (CTA), isoleucine codon (ATA) and proline codon (CCC), on the level of translation and consecutively on the decrease of the amount and quality of the expressed protein in E. coli are described in Kane J F, Current Opinion in Biotechnology, 6:494-500 (1995). There is a similar impact of individual rare codons if they occur in different parts of the gene.

The GC rich regions also have an impact on the translational efficiency in E. coli if a stable double stranded RNA is formed in the mRNA secondary structure. This impact is the highest when the GC rich regions of mRNA are found either in the RBS, or in the direct proximity of the RBS or also in the direct proximity of the start codon (Makrides S C, Microbiological Reviews, 60:512-538 (1996); Baneyx F, Current Opinion in Biotechnology, 10:411-421 (1999)).

There are known several methods for the prediction of the secondary structure and calculating minimal free energy of individual RNA molecule which is supposed to be the basic rule for the most stable/most probable structure (SantaLucia J Jr and Turner D H, Biopolymers, 44:309-319 (1997)). The reliable algorithms for the prediction of the correct secondary structure are not known, with the exception of some cases. There has been no evidence for the quantitative correlation with the expression level (Smit M H and van Duin J. J. Mol. Biol., 244, 144-150 (1994)). It is still impossible to predict the tertiary structures of RNA (Tinoco, I. and Bustamante C., J. Mol. Biol, 293:271-281 (1999)).

The increase of the expression level after the optimization of DNA sequence in the TIR region, in the RBS region and in the region between the start codon and the RBS region is described in McCarthy J E G and Brimacombe R, Trends Genet 10:402-407 (1994). In this case the expression level increased due to more efficient translation initiation and its smooth continuation in the mRNA coding region.

The production of adequate amounts of hG-CSF for performing the in vitro biological studies by expression in E. coli is described in Souza L M et al, Science 232:61-65 (1986) and in Zsebo K M et al, Immunobiology 172:175-184 (1986). The hG-CSF expression level was lower than 1%.

The U.S. Pat. No. 4,810,643 discloses the use of synthetic gene coding for hG-CSF which was first of all constructed on the basis of replacement of E. coli rare codons with the E. coli preference codons. The combination with thermoinducible phage lambda promoter led to the expression level of 3 to 5% of hG-CSF regarding the total cellular proteins. This level is not sufficient for the economical large-scale production of hG-CSF.

8-10% accumulation of hG-CSF to total cellular proteins was reached by changing the first four codons in the 5' end region of hG-CSF as is described in Wingfield P et al, Biochem. J, 256:213-218 (1988).

The expression of hG-CSF in E. coli with the yield up to 17% of hG-CSF to total cellular bacterial proteins is described in Devlin P E et al, Gene 65:13-22 (1988). Such yield was reached with partial optimization of DNA sequence in the 5' end of the G-CSF coding region (codons coding for the first four amino acids) whereby the GC region was replaced with an AT region and a relatively strong lambda phage promoter was used. This expression level is not very high which leads to lower production yields and is less economical in the large-scale production.

The use of a synthetic gene and the expression level of about 30% are described in Kang S H et al, Biotechnology letters, 17(7):687-692 (1995). This level was attained by the introduction of E. coli preference codons, by the modifications in the TIR region, and with the additional modifications of codon sets whereby the 3' end of the gene was not essentially changed. Thus, for attaining the stated expression level the changes of the gene in the TIR region were needed and the expression level did not exceed 30%.

The U.S. Pat. No. 5,840,543 describes the synthetic gene coding for hG-CSF which was constructed by the introduction of AT rich regions at the 5' end of the gene and with the replacement of E. coli rare codons with E. coli preference codons. Under the control of the Trp promoter, expression with the yield of 11% hG-CSF to total cellular proteins was reached. On the other hand, the addition of leucine and threonine or their combination into the fermentation medium (where the bacteria were cultivated) led to the accumulation of up to 35% of hG-CSF regarding total cellular proteins. Such expression level was therefore reached by the addition of amino acids into the fermentation medium which is an additional cost in the process for production of hG-CSF and is not economical for the industrial production. Only optimization of the gene coding for hG-CSF did not enable a higher expression level of hG-CSF.

The highest accumulation of hG-CSF regarding total cellular proteins found in the prior art is described in v Jeong et al, Protein Expression and Purification 23,:311-318 (2001) and is 48%. Such accumulation was obtained by the changes in the N-terminal end and by the induction with 1 mM IPTG.

In general, there are no reports on possible predictions of the expression level of native human genes in prokaryotic organisms, e.g. bacterium E. coli. The described expression levels are relatively low or difficult to detect even when the expression plasmids with strong promoters, e.g. from lambda or T7 phage are used. From the prior art literature it can be gathered that many parameters (rare codons or their clustering; GC base pairs rich regions, unfavorable mRNA secondary structures, unstable mRNA) have an impact on the accumulation of a human protein in E. coli.

Until now, there has been no entirely developed rule known on how to combine codons in order to obtain secondary or tertiary mRNA structures which are optimal for expression. Although there exist some mathematical and structural models for predicting and thermodynamic stability of secondary structures, they are too unreliable to predict the secondary structures. On the other hand, there are no such models for predicting the tertiary structures. These currently accessible models therefore do not enable the prediction of the impact of the codons on the expression level.

There are no reports in either the patent or the scientific literature on the more efficient way for solving the problem of low expression level of the gene coding for hG-CSF in *E. coli*.

SUMMARY OF THE INVENTION

It is thus an object of the present invention to provide a DNA sequence coding for hG-CSF or biologically active G-CSF, which DNA sequence enables an improved expression level (accumulation) in *E. coli*, and to provide a process for the construction of such a DNA sequence.

The above and other objects are addressed by a DNA sequence according SEQ ID NO:1, and by a process for the construction of such a DNA sequence as disclosed herein. The present invention also provides an expression plasmid, an expression system, a process for the expression of hG-CSF, and a process for the manufacture of a pharmaceutical. Preferred embodiments of these and other aspects of the invention are also disclosed herein.

A significant feature of the present invention is that the use of a synthetic gene coding for hG-CSF enables one to attain an expression level (accumulation) in *E. coli* being equal to or higher than 52% of recombinant hG-CSF regarding the total proteins in *E. coli* Preferably, an expression plasmid containing a strong T7 promoter is used for the expression. The synthetic gene coding for hG-CSF is constructed by using a complex combination of two methods which enable the construction of an optimized synthetic gene (coding for hG-CSF) for its expression in *E. coli*. The first method includes the replacement of some rare *E. coli* codons which are unfavorable for expression in *E. coli* by *E. coli* preference codons for which are more favorable for expression in *E. coli*. The second method includes the replacement of some GC rich regions by AT rich regions. Some parts of the synthetic gene of the present invention are constructed by using one of the two methods, for some parts; the combination of the two methods is used, whereas some parts of the gene are not changed. In the construction procedure of the synthetic gene coding for hG-CSF, which is also the subject of the present invention, the non coding (5'-untranslated) regions are preferably not changed. Advantageously, this means that there are no modifications in either the translation initiation region (TIR) or in the ribosome binding site (RBS), or in the region between the start codon and RBS.

BRIEF DESCRIPTION OF THE DRAWINGS

FIG. 2 shows SEQ ID NO:3, the DNA sequence of the native gene sequence coding for hG-CSF (FIG. 2A) (Gen-Bank: NM_000759) and SEQ ID NO:1, the DNA sequence of the optimized (Fopt5) gene coding for hG-CSF (FIG. 2B). The bases which differ from native gene are bolded.

FIG. 3 shows an SDS-PAGE analysis of samples of proteins obtained from the expression of native hG-CSF DNA sequence (lanes 1 to 4) and of optimized (Fopt5) gene coding for hG-CSF (lanes 6 and 7) in induced and noninduced cultures of *E. coli*, as evaluated by dye staining (FIG. 3A) and by Western blot using antibody specific for hG-CSF protein (FIG. 3B).

DESCRIPTION OF THE INVENTION AND THE PREFERRED EMBODIMENTS THEREOF

Figure 1:
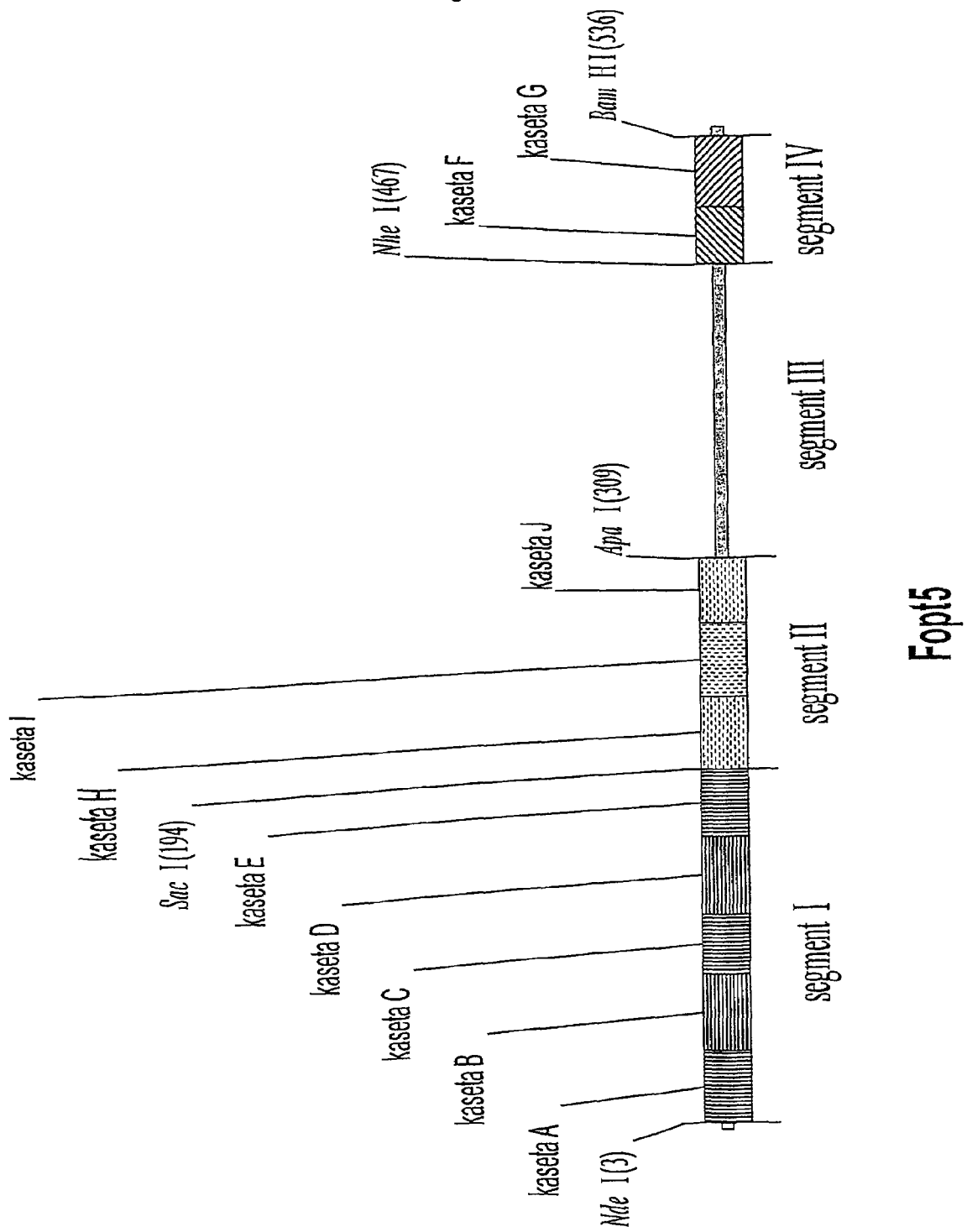
FIG. 1 schematically shows an optimized construction of a synthetic gene coding for hG-CSF according to a preferred embodiment of the present invention.

It has been found that the problem with the low expression level of the gene coding for hG-CSF in *E. coli* can be solved by the optimization of the gene sequence coding for hG-CSF. The native gene coding for hG-CSF, defined by SEQ ID NO:3, is changed, leading to the construction of a particular synthetic gene coding for hG-CSF. The particular synthetic gene is defined by the DNA sequence of SEQ ID NO: 1 or by a nucleotide sequence comprising suitable modifications of SEQ ID NO: 1 or of the native hG-CSF gene sequence, SEQ ID NO:3.

In comparison with the data described in the art, surprisingly high expression level can be obtained according to the present invention.

The term 'hG-CSF', as used herein, refers to human granulocyte-colony stimulating factor, comprising the recombinant hG-CSF obtained by expression in *E. coli*.

The synthetic gene encoding hG-CSF of the present invention was obtained by introducing changes in the nucleotide sequence of the gene encoding the native hG-CSF. Thus the amino acid sequence was not changed and remained identical to the native hG-CSF.

The present invention further comprises a process for the expression of the synthetic gene in *E. coli* and concerns the level of expression of the synthetic gene.

The term 'expression level', as used herein, refers to the proportion of hG-CSF obtained after the heterologous expression of the gene encoding hG-CSF regarding the total cellular proteins after expression. The expression level may be quantified from the quantification of appropriately separated proteins after expression, e.g. quantifying the staining of protein bands separated by SDS-PAGE.

The term 'heterologous expression', as used herein, refers to the expression of the genes which are foreign to the organism in which the expression occurs.

The term 'homologous expression', as used herein, refers to the expression of the genes which are proper to the organism in which the expression occurs.

The term 'preference codons', as used herein, refers to the codons used by an individual organism (e.g. *E. coli*) for the production of most mRNA molecules. The organism uses these codons for expressing genes with high homologous expression.

The term 'rare codons' as used herein, refers to the codons used by an individual organism (e.g. *E. coli*) only for expressing genes with low expression level. These codons are rarely used in the organism (low homologous expression).

The term 'GC rich regions', as used herein, refers to the regions in the gene where the bases guanine (G) and cytosine (C) prevail.

The term 'AT rich regions', as used herein, refers to the regions in the gene, where the bases adenine (A) and thymine (T) prevail.

The term 'synthetic gene', as used herein, refers to the gene prepared from short double stranded DNA fragments which are composed of synthetic complementary oligonucleotides.

This synthetic gene differs from the native gene (e.g., cDNA) only in the nucleotide sequence, while the amino acid sequence remains unchanged. The synthetic gene is obtained by the techniques of the recombinant DNA technology.

The term 'native gene', as used herein, refers to the DNA sequence of a gene which is identical to the native DNA sequence.

The term 'segment', as used herein, refers to the parts of the genes which are bounded by single restriction sites on both ends. These sites serve as subcloning sites for the synthetically constructed parts of the gene. In the following the restrictions sites are numbered according to the nucleotide position in the 5'-3' direction from the start codon.

The term 'segment I', as used herein, refers to the 5' end of the gene encoding hG-CSF, defined by SEQ ID NOS:1, 2, or 3, between the nucleotide positions 3 and 194 (notably the restriction sites NdeI (3) and SacI (194)), i.e. 191 bp long sequence. Segment I may be de novo synthesized.

The term 'segment II', as used herein, refers to the part of the gene for hG-CSF, defined by SEQ ID NOS:1, 2, or 3, between the nucleotide positions 194 and 309 (notably the restriction sites SacI (194) and ApaI (309)), i.e. 115 bp long central part of the gene. Segment II may be de novo synthesized.

The term 'segment III', as used herein, refers to the part of the gene for hG-CSF, defined by SEQ ID NOS:1, 2, or 3, between the nucleotide positions 309 and 467 (notably the restriction sites ApaI (309) and NheI (467)), i.e. 158 bp long part of the gene where the native DNA sequence for hG-CSF is preserved with the exception of codons for Arg148 and Gly150.

The term 'segment IV', as used herein, refers to the 3' terminal end of the gene encoding hG-CSF, defined by SEQ ID NOS:1, 2, or 3, between the nucleotide positions 467 and 536 (notably the restriction sites NheI (467) and BamHI (536)), i.e. 69 bp long terminal part of the gene. Segment IV may be de novo synthesized.

The synthetic gene encoding hG-CSF, one embodiment of which is defined by SEQ ID NO:1, of the present invention is constructed by the combination of the following methods:
  replacement of *E. coli* rare codons with *E. coli* preference codons: in the segment II (between restriction sites SacI (194) and ApaI (309)) and in the segment IV (between restriction sites NheI (467) and BamHI (536))of SEQ ID NO:3.
  replacement of GC rich regions with AT rich regions, whereby the rarest *E. coli* codons are replaced, but mostly not with the *E. coli* preference codons: in the segment I (between restriction sites NdeI (3) and SacI (194)) of SEQ ID NO:3.
  completely unchanged native sequence of 46 codons (between CCC for Pro102 and CGC for Arg147) in the segment III of SEQ ID NO:3.
  replacement of two *E. coli* rare codons (CGG→CGT (Arg148) and GGA→GGT (Gly150)) at the terminal end of the segment III of SEQ ID NO:3.

Optimization of the gene coding for hG-CSF of the present invention does not include changes in the TIR, RBS and in the regions between the start codons and RBS.

The synthetic gene of the present invention encoding hG-CSF, defined by SEQ ID NO:1, enables expression of the constructed synthetic gene encoding hG-CSF with the expression level in *E. coli* equal to or higher than 52%. Furthermore, the expression level of about 55% or even about 60% can also be obtained. High expression level of the synthetic gene coding for hG-CSF, defined by SEQ ID NO:1, of the present invention enables high yields of hG-CSF production, faster and simpler purification and isolation of heterologous hG-CSF, easier in-process control, and the whole production process is more economical. Therefore, the efficient production of hG-CSF in industrial scale is enabled. The produced hG-CSF is suitable for clinical use in medicine.

The construction of the synthetic gene of the present invention, defined by SEQ ID NO:1, begins with the initial preparation of the hG-CSF native gene and of the plasmids. Gene coding for native hG-CSF can be of human origin, such as the gene defined by SEQ ID NO:3, but the same principle can be used for every gene which is homologous in the regions which comprise single restriction sites which are used for subcloning of de novo synthesized gene segments. The plasmid for mutagenesis was chosen according to its ability to be capable of enabling the successive introduction of point mutations. Selection or enrichment of the plasmids containing desired mutation was obtained by using an additional selection primer that changed unique restriction site EcoRI into EcoRV or vice-versa (Transformer™ Site-Directed Mutagenesis Kit (Clontech)). The gene and the plasmid are constructed in such a way that the introduction of point mutation by cassette mutagenesis is possible.

After the initial preparation of the native gene coding for hG-CSF, defined by SEQ ID NO:3, and of plasmids the optimization of the native gene coding for hG-CSF is performed. This means that the synthetic gene coding for hG-CSF, defined by SEQ ID NO:1, is constructed. The optimization begins with the division of the native gene coding for hG-CSF (SEQ ID NO:3) into four (I, II, III, and IV) segments, which are or will be separated with single restriction sites after the oligonucleotide mutagenesis. Changes are introduced in individual segments. In some individual segments, changes in the gene sequence are introduced, whereas in certain segments the gene is not changed (FIG. 1). The optimized synthetic gene coding for hG-CSF (SEQ ID NO:1) therefore consists of a partially preserved native sequence (segment III) of SEQ ID NO:3 and of 5' and 3' coding regions which are synthesized de novo (segments I, II, and IV).

The changes in the individual segments:

Segment I: Replacement of *E. coli* rare codons with *E. coli* preference codons and replacement of GC rich regions with AT rich regions Italic: GC/AT rich replacement; Italic and underlined: rare/preference codon replacements and GC/AT rich replacement; underlined: rare/preference codon replacements; Gly101 (GGT→GGG) introduction of ApaI (309) restriction site.

Thr2 (ACC→ACA), Pro3 (CCC→CCA), Gly5 (GGC→GGT) Pro6 (CCT→CCA), Ala7 (GCC→GCT), Ser8 (AGC→TCT), Ser9 (TCC→TCT), Pro11(CCC→CCG), Gln12 (CAG→CAA), Phe14 (TTC→TTT), Leu16 (CTC→TTG), Lys17(AAG→AAA), Cys18 (TGC→TGT), Glu20(GAG→GAA), Val22 (GTG→GTT), Arg23(AGG→CGT), Lys24(AAG→AAA) Ile25 (ATC→ATT), Gln26 (CAG→CAA), Gly27 (GGC→GGT), Gly29 (GGC→GGT), Ala31 (GCG→GCT), Leu32 (CTC→TTA), Gln33 (CAG→CAA), Glu34(GAG→GAA), Lys35(AAG→AAA), Ala38 (GCC→GCA), Thr39 (ACC→ACT), Tyr40 (TAC→TAT), Lys41(AAG→AAA), Cys43 (TGC→TGT), His44 (CAC→CAT), Pro45 (CCC→CCA), Glu46(GAG→GAA), Glu47(GAG→GAA), Val49 (GTG→GTT), Leu51 (CTC→TTA), Gly52(GGA→GGT), His53 (CAC→CAT), Gly56 (GGC→GGT), Ile57 (ATC→ATT), Pro58(CCC→CCG), Pro61 (CCC→CCT)

Segment II: Replacement of *E. coli* rare codons with *E. coli* preference codons.

Cys65 (TGC→TGT), Pro66(CCC→CCG), Ala69(GCC→GCG), Leu76(TTG→CTG), Leu79(CTC→CTG), Gly82 (GGC→GGT), Leu83(CTT→CTG), Phe84 (TTC→TTT), Leu85(CTC→CTG), Tyr86 (TAC→TAT), Gly88(GGG→GGT), Leu89(CTC→CTG), Ala92(GCC→GCG), Gly95(GGG→GGC), Ile96(ATA→ATT), Pro98(CCC→CCG), Glu99(GAG→GAA), Leu100(TTG→CTG), Gly101 (GGT→GGG)

Segment III: Replacement of two *E. coli* rare codons situated just before the restriction site NheI Arg148(CGG→CGT), Gly150(GGA→GGT)

Segment IV: Replacement of a long cluster of *E. coli* rare codons at the terminal end of the gene with *E. coli* preference codons.

Gln159 (CAG→CAA), Ser160 (AGC→TCT), Phe161 (TTC→TTT), Glu163(GAG→GAA), Val164 (GTG→GTT), Ser165(TCG→AGC), Tyr166 (TAC→TAT), Arg167 (CGC→CGT), Leu169(CTA→CTG), Arg170 (CGC→CGT), His171 (CAC→CAT), Leu172(CTT→CTG), Ala173 (GCG→GCT), Pro175(CCC→CCG)

After the construction of the synthetic gene coding for hG-CSF the optimized synthetic gene is subcloned in the final plasmid vector suitable for the expression in *E. coli* Preferably, the plasmid vector is selected from the group of pET vectors (available from Novagen). These vectors contain a strong T7 promoter. More preferably the plasmid vector pET3a comprising an ampicilline resistance gene, and particularly the plasmid vector pET9a comprising a kanamycin resistance gene is used. The expression plasmid which is thereby constructed is then transformed into an appropriate *E. coli* production strain. Preferably, the *E. coli* production strain is selected from the group of strains which carry on the chromosome or expression plasmid gene for T7 RNA polymerase. Most preferably, *E. coli* BL21 (DE3) is used.

The procedure is continued with the preparation of inoculum and with the fermentation process in a suitable culture medium. Preferably, IPTG is used for induction, suitable at a concentration in the range of about 0.1 mM to about 1 mM. Preferably at a concentration of about 0.3 to 0.6 mM. The fermentation, can be performed at about 37° C., but is preferably performed below 30° C., more preferably at about 20 to 30° C., particularly at about 25° C. Performing the fermentation process at such a lower temperature than conventionally used can advantageously assist in the accumulation of precursor molecules of biologically active G-CSF in inclusion bodies.

The fermentation process may be performed in the presence or in the absence of the antibiotic that corresponds to the resistance gene is inserted into the plasmid vector, e.g. with ampicilline or kanamycin at an appropriate concentration or in the absence thereof. It has also been found that the fermentation and thus the accumulation of hG-CSF was highly effective without a selection pressure.

The accumulated heterologous hG-CSF is found in the inclusion bodies and is suitable for the renaturation process and use in the isolation procedures.

Suitable techniques for the isolation and/or purification of the hG-CSF or biologically active G-CSF protein are known to the person skilled in the art and can be used, e.g., classical or expanded-bed chromatography using any of well known principles, e.g., ion-exchange, hydrophobic-interaction, affinity or size-exclusion, as well as continuous and batch-mode extractions using appropriate matrices or solutions. The preferred technique is immobilised metal affinity chromatography (IMAC), as it enables a highly efficient preparation of pure and biologically active protein in high yield and under native conditions.

The isolated and/or purified hG-CSF or biologically active G-CSF obtained according to the present invention can be used in a process for the manufacture of a pharmaceutical composition containing it as an effective ingredient. The pharmaceutical composition comprises an amount of hG-CSF or biologically active G-CSF that is therapeutically effective to treat a desired disease in a patient.

Suitable pharmaceutically acceptable carrier or auxiliary substances include suitable diluents, adjuvants and/or carriers useful in G-CSF therapy.

Biologically active G-CSF which was obtained by using the process of the present invention can be used for preparation of medicaments, which are indicated for the indications selected from the group, which comprises: neutropenia and neutropenia-related clinical sequelae, reduction of hospitalisation for febrile neutropenia after chemotherapy, mobilisation of hematopoietic progenitor cells, as alternative to donor leukocyte infusion, chronic neutropenia, neutropenic and non-neutropenic infections, transplant recipients, chronic inflammatory conditions, sepsis and septic shock, reduction of rist, morbidity, mortality, number of days of hospitalisation in neutropenic and non-neutropenic infections, prevention of infection and infection-related complications in neutropenic and non-neutropenic patients, prevention of nosocomial infection and to reduce the mortality rate and the frequency rate of nosocomial infections, enteral administration in neonates, enhancing the immune system in neonates, improving the clinical outcome in intensive care unit patients and critically ill patients, wound/skin ulcers/burns healing and treatment, intensification of chemotherapy and/or radiotherapy, pancytopenia, increase of anti-inflammatory citokines, shortening of intervals of high-dose chemotherapy by the prophylactic employment of filgrastim, potentiation of the anti-tumour effects of photodynamic therapy, prevention and treatment of illness caused by different cerebral disfunctions, treatment of thrombotic illness and their complications and post irradiation recovery of erythropoiesis.

It can be also used for treatment of all other illnesses, which are indicative for G-CSF.

The pharmaceutical composition containing the pure and biologically active G-CSF obtained by the process of the invention can thus be administered, in a manner known to those skilled in the art, to patients in a therapeutically amount which is effective to treat the above mentioned diseases.

The present invention will be explained in more detail by the examples below and by reference to the accompanying drawings, which examples and drawings are however merely illustrative and shall not considered as limiting the present invention.

EXAMPLES

Example 1

Construction of the Optimal Gene: Fopt5

Example 1a

The Initial Gene and Plasmid Preparations

The gene coding for hG-CSF, defined by SEQ ID NO:3, was amplified from BBG13 (R&D) with the PCR method, which was also used to introduce by using the start oligonucleotides the restriction sites NdeI and BamHI at the start and terminal end of the gene. The gene was then incorporated in the plasmid pCytexΔH,H (see the description below) between the restriction sites NdeI and BamHI. All other optimization steps for the expression of the gene in *E. coli* were also performed in this plasmid.

During the initial gene preparation the EcoRV restriction site was annihilated (oligo M20z108, defined by SEQ ID NO:4) by point mutation. This was performed with the aim to ensure the possibility of introduction of (individual) mutations by using the oligonucleotide-directed mutagenesis in the plasmid pCytexΔH,H with the kit Transformer™ Site-Directed Mutagenesis Kit (Clontech). The selection of mutants in the plasmid pCytexΔH,H-G-CSF via the restriction sites EcoRI/EcoRV was therefore possible.

The starting plasmid pCYTEXP1 (Medac, Hamburg) was reconstructed in a way to enable the constitutive expression. This was performed by the excision of the part of the gene coding for cI857 repressor between both restriction sites HindIII. The obtained plasmid was named pCytexΔH,H.

The oligonucleotide for the annihilation of EcoRV site from the gene coding for hG-CSF:

```
M20z108    5'-CCT GGA AGG AAT ATC CCC CG-3'
           (SEQ ID NO:4)
```

Example 1b

Codon Optimization (FIG. 1)

In a first optimization step the synthetic gene between the restriction sites NdeI and SacI was constructed by ligation of five cassettes (A, B, C, D, E) which were composed of complementary oligonucleotides. This synthetic part of the gene represents the segment I. With the segment I, the part of the native gene for hG-CS F (SEQ ID NO:3) between the restriction sites NdeI and SacI was replaced. This was performed by the excision of the first part of the gene between the restriction sites NdeI and SacI, and replacement with the synthetically prepared cassette. The process was performed in two steps. In the first step, the cassette A, defined by SEQ ID NOS:5 and 6, was ligated to the NdeI site and the cassette E, defined by SEQ ID NOS:13 and 14, was ligated to the SacI site. After 16 hours at 16° C. the ligation mixture was precipitated with ethanol to remove the excess of unbound oligonucleotides. In a second step the central part of the whole cassette (cassettes B, defined by SEQ ID NOS:7 and 8, C, defined by SEQ ID NOS:9 and 10,and D, defined by SEQ ID NOS:11 and 12,) from the three previously ligated complementary oligonucleotides was added and the ligation was performed for 16 hours at 16° C.

In a second optimization step, two critical codons for *E. coli*, located in segment III, namely, CGG→CGT (Arg148) and GGA→GGT (Gly150), were replaced by using oligonucleotide-directed mutagenesis (Transformer™ Site-Directed Mutagenesis Kit (Clontech)).

In the third optimization step the segment IV was constructed in a similar way as the segment I with the exception of intermediate ethanol precipitation. The segment IV represents the last part of the gene between the restrictions sites NheI and BamHI and is composed of two pairs of complementary oligonucleotides (cassettes F, defined by SEQ ID NOS:16 and 17, and G, defined by SEQ ID NOS:18 and 19).

In the fourth step of optimization the rare codon coding for Ile96 was replaced (ATA→ATT) (segment II) by using the oligonucleotide-directed mutagenesis (Transformer™ Site-Directed Mutagenesis Kit (Clontech)) and the restriction site for ApaI (309) (GGT→GGG (Gly101)) was introduced at the 3' end of the segment II.

ApaI restriction site was then used in the fifth optimization step with the aim to replace the native gene between SacI and ApaI with the synthetic DNA (segment II). This synthetic DNA is composed of three pairs of complementary oligonucleotides (cassette H, defined by SEQ ID NOS:21 and 22, I, defined by SEQ ID NOS:23 and 24, and J, defined by SEQ ID NOS:25 and 26). This was performed similarly as in the first step with the later addition of the cassette I.

1st Optimization Step:

Complementary pairs of oligonucleotides (NdeI-SacI; Segment I in FIG. 1):

Cassette A: Composed of complementary oligonucleotides zg1os1 in sp1 os2:

```
zg1os1
5' TAT GAC ACC ACT GGG TCC AGC TTC TTC TCT GCC GCA
AAG 3'
(SEQ ID NO:5)

sp1os2
5' GCA GAG AAG AAG CTG GAC CCA GTG GTG TCA 3'
(SEQ ID NO:6)
```

Cassette B: Composed of complementary oligonucleotides zg2os3 in sp2os4:

```
zg2os3
5' CTT TCT GTT GAA ATG TTT AGA ACA AGTTCG TAA AAT
TCA AG 3'
(SEQ ID NO:7)

sp2os4
5' GAA CTT GTT CTA AAC ATT TCA ACA GAA AGC TTT
GCG 3'
(SEQ ID NO:8)
```

Cassette C: Composed of complementary oligonucleotides zg3os5 in sp3os6:

```
zg3os5
5' GTG ATG GTG CAG CTT TAC AAG AAA AAC TGT GTG 3'
(SEQ ID NO:9)

sp3os6
5' GTT TTT CTT GTA AAG CTG CAC CAT CAC CTT GAA TTT
TAC 3'
(SEQ ID NO:10)
```

Cassette D: Composed of complementary oligonucleotides zg4os7 in sp4os8:

```
zg4os7
5' CAA CTT ATA AAC TGT GTC ATC CAG AAG AAC TGG TTC
TGT TAG 3'
(SEQ ID NO:11)

sp4os8
5' CAG TTC TTC TGG ATG ACA CAG TTT ATA AGT TGC ACA
CA 3'
(SEQ ID NO:12)
```

Cassette E: Composed of complementary oligonucleotides zg5os9 in sp5os10:

```
zg5os9
5' GTC ATT CTC TGG GTA TTC CGT GGG CTC CTC TGA
GCT 3'
(SEQ ID NO:13)

sp5os10
5' CAG AGG AGC CCA CGG AAT ACC CAG AGA ATG ACC TAA
CAG AAC 3'
(SEQ ID NO:14)
```

2$^{nd}$ Optimization Step: Oligonucleotides for the replacement of the most critical codons by using the oligonucleotide-directed mutagenesis replacement CGG→CGT (Arg 148) and GGA→GGT (Gly 150)

```
m38os16
5' CTC TGC TTT CCA GCG CCG TGC AGG TGG GGT CCT GGT
TG 3'
(SEQ ID NO:15)
```

3$^{rd}$ Optimization Step: Complementary pairs of nucleotides (NheI-BamHI; Segment IV on FIG. 1):

Cassette F: Composed of complementary nucleotides zg6os11 in sp6os12:

```
zg6os11
5' CTA GCC ATC TGC AAT CTT TTC TGG AAG TTA G 3'
(SEQ ID NO:16)

sp6os12
5' ACG ATA GCT AAC TTC CAG AAA AGA TTG CAG ATG
G 3'
(SEQ ID NO:17)
```

Cassette G: Composed of complementary oligonucleotides zg7os13 in sp7os14:

```
zg7os13
5' CTA TCG TGT TCT GCG TCA TCT GGC TCA GCC GTG ATA
AG 3'
(SEQ ID NO:18)

sp7os14
5' GAT CCT TAT CAC GCG CTG AGC CAG ATG ACG CAG AGA
AC 3'
(SEQ ID NO:19)
```

4$^{th}$ Optimization Step: Oligonucleotides for the introduction of ApaI (309) (GGT→GGG (Gly101)), and the replacement of the rare codon ATA→ATT (Ile96) by using the oligonucleotide-directed mutagenesis insertion of ApaI (309) (GGT→GGG (Gly101)), and replacement ATA→ATT (Ile 96):

```
Apaios15
5' GCC CTG GAG GGG ATT TCC CCC GAG TTG GGG CCC ACC
TTG GAC AC 3'
(SEQ ID NO:20)
```

5. Optimization Step: Complementary pairs of oligonucleotides (SacI-ApaI; Segment II in FIG. 1):

Cassette H: Composed of complementary oligonucleotides zg8os18 in sp8os19:

```
zg8os18
5' CCT GTC CGA GCC AGG CGC TGC AGC TGG CAG GCT CCC
TGA G 3'
(SEQ ID NO:21)

sp8os19
5' CCT GCC AGC TGC AGC GCC TGG CTC GGA CAG GAG
CT 3'
(SEQ ID NO:22)
```

Cassette I: Composed of complementary oligonucleotides zg9os20 in sp9os21:

```
zg9os20
5' CCA ACT GCA TAG CGG TCT GTT TCT GTA TCA GGG TCT
GCT G 3,
(SEQ ID NO:23)

sp9os21
5' CTG ATA CAG AAA CAG ACC GCT ATG CAG TTG GCT CAG
GCA G 3,
(SEQ ID NO:24)
```

Cassette J: Composed of complementary oligonucleotides zg10os22 in sp10os23:

```
zg10os22
5' CAG GCG CTG GAA GGC ATT TCC CCG GAA CTG GGG
CC 3'
(SEQ ID NO:25)

sp10os23
5' CCA GTT CCG GGG AAA TGC CTT CCA GCG CCT GCA GCA
GAC C 3'
(SEQ ID NO:26)
```

Example 2

Expression of the Synthetic Gene Coding for hG-CSF in *E. coli*

The optimized gene Fopt5, defined by SEQ ID NO:1, was excised from the plasmid pCyΔH,H with the restriction enzymes NdeI and BamHI and the gene was then subcloned in the final expression plasmid pET3a (Novagen, Madison USA), which contains an ampicilline resistance gene, which was then transformed into the production strain *E. coli* BL21 DE3).

The cultures were prepared on a shaker at 160 rpm for 24 hours at 25° C. or 15 hours at 42° C.:

in LBG10/amp100 medium (10 g/l tryptone, 5 g/l yeast extract, 10 g/l- NaCl, 10 g/l glucose, 100 mg/l ampicillin). The induction was performed with the addition of IPTG to the final concentration of 0.4 mM.

The cultures were prepared on a shaker for 24 hours at 160 rpm at 25° C.:

in GYSP/amp100 medium (20 g/l phytone, 5 g/l yeast extract, 10 g/l NaCl, 10 g/l glucose, metals in traces, 100 mg/l ampicillin). The induction was performed with the addition of IPTG into the medium to the final concentration of 0.4 mM.

in LYSP/amp100 medium (20 g/l phytone, 5 g/l yeast extract, 10 g/l NaCl, 6 g/l glycerol, 4 g/l lactose, metals in traces, 100 mg/l ampicillin). The induction was performed with the addition of lactose into the medium.

The inoculum was prepared in LBG/amp100 medium (10 g/l tryptone, 5 g/l yeast extract, 10 g/l NaCl, 2.5 g/l glucose) and 100 mg/l ampicillin at 25° C., 160 rpm overnight.

For analysis 8 ml of the culture was centrifuged at 5000 rpm. The pellets were then resuspended in 10 mM Tris HCl/pH=8.0 in a proportion of 0.66 ml buffer added to calculated 1 unit $OD_{600nm}$. The loaded amounts were thereby equalized. Namely, the final $OD_{600nm}$ of the cultures in the stated examples were not equal. The samples were mixed in the proportion of 3:1 with 4×SDS—sample buffer with DTT (pH=8.7) and heated 10 minutes at 95° C., centrifuged and loaded onto the gel.

Figure 4:
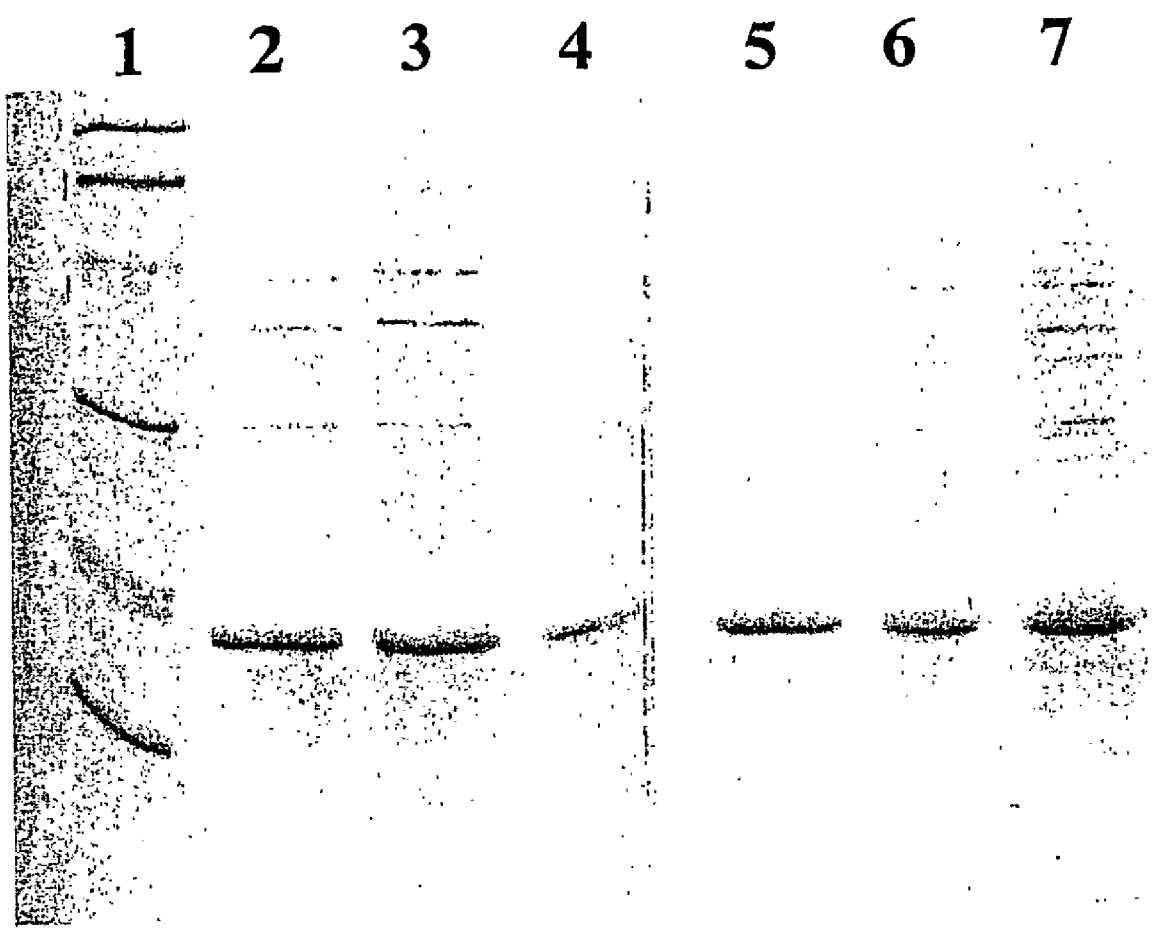
FIG. 4 shows an SDS-PAGE analysis of samples of proteins obtained from the expression of optimized (Fopt5) gene coding for hG-CSF in induced culture of *E. coli*, as evaluated by dye staining.

Samples of various expression examples, using the optimized gene construction and the conventional hG-CSF cDNA, were compared by SDS-PAGE evaluations. The SDS-PAGE conditions were as follows, giving results are shown by FIGS. 3 and 4.

FIG. 3 A: SDS-PAGE (4% stacking, 15% separating; stained with Coomassie brilliant blue) of the samples of the proteins from the induced and noninduced cultures of production strains *E. coli* BL21 (DE3) with the expression plasmid pET3a at 25° C. and 42° C. The cultures were cultivated in the LBG10/amp100 medium.

Legend:

Load 1: BL21 (DE3) pET3a-hG-CSF non-induced at 25° C. (10 µl) (no traces of hG-CSF)

Load 2: BL21 (DE3) pET3a-hG-CSF induced with IPTG at 25° C. (10 µl) (slight trace hG-CSF)

Load 3: BL21 (DE3) pET3a-hG-CSF non-induced at 42° C. (10 µl) (no traces hG-CSF)

Load 4: BL21 (DE3) pET3a-hG-CSF induced with IPTG at 42° C. (10 µl) (under 1% hG-CSF)

Load 5: standard filgrastim 0.3 µg for Coomassie brilliant blue

Load 6: BL21 (DE3) pET3a-Fopt5 non-induced at 25° C. (5 µl) (6% hG-CSF)

Load 7: BL21 (DE3) pET3a-Fopt5 induced with IPTG at 25° C. (5 µl) (over 50% hG-CSF)

FIG. 3 B: Detection with antibodies (Western blot); primary rabbit antibodies; secondary goat anti-rabbit IgG antibodies conjugated with horseradish peroxidase, substrate β-naphthol.

The samples for the detection with antibodies were loaded in the same amount and in the same sequence as at SDS-PAGE (FIG. 3a) with the exception of the standard which load was 0.08 µg.

FIG. 4: SDS-PAGE (4% stacking, 15% separating; stained with Coomassie brilliant blue) samples of proteins from induced culture of the production strain *E. coli* BL21 (DE3) with the expression plasmid pET3a at 25° C. The cultures were cultivated in GYSP/amp100 and LYSP/amp100 medium.

Legend:

Load 1: LMW (BioRad)

Load 2: BL21 (DE3) pET3a/P-Fopt5, the culture cultivated in LYSP/amp100; (60% hG-CSF)

Load 3: BL21 (DE3) pET3a/P-Fopt5, the culture cultivated in LYSP/amp100; (over 54% hG-CSF)
    Load 4: rhG-CSF (0.6 µg)

Load 5: rhG-CSF (1.5 µg)

Load 6: BL21 (DE3) pET3a/P-Fopt5, the culture cultivated in GYSP/amp100 (4 µl); (55% hG-CSF)

Load 7: BL21 (DE3) pET3a/P-Fopt5, the culture cultivated in GYSP/amp100 (5 µl); (52% hG-CSF)

The content (%) of accumulated hG-CSF found in the form of inclusion, bodies for the native and optimized gene are described in Table 1.

TABLE 1

Comparison of the accumulation levels of hG-CSF for the native and the optimized gene (Fopt5)

| | | hG-CSF content (%) in total proteins cultivation and induction conditions | | |
|---|---|---|---|---|
| | | native gene coding for hG-CSF | | optimized gene Fopt5 |
| | | cultivation temperature | | |
| Expression system | | 25° C. | 42° C. | 25° C. |
| *E. coli* BL21 (DE3) pET3a | medium LBG10/amp100 0.4 mM IPTG | traces | <1% | >40% |
| *E. coli* BL21 (DE3) pET3a | medium GYSP/amp100 0.4 mM IPTG | <1% | <1% | >52% |
| *E. coli* BL21 (DE3) pET3a | medium LYSP/amp100 | <1% | <1% | >52% |

The indicated values for hG-CSF contents are obtained by the densitometric analysis of SDS-PAGE gels stained with Coomassie brilliant blue in the case of Fopt5 (FIG. 3A and FIG. 4) and by using the detection with antibodies (in the case of unoptimized gene (FIG. 3B). In the case of Fopt5 the relative amount of hG-CSF for the estimation of expression level was determined with the profile analysis (program Molecular analyst; BioRad) of the gels by using the apparatus Imaging densitometer Model GS670 (BioRad).

The results show a drastically improved expression level when the optimized synthetic gene Fopt5 was used.

Example 3

Expression of the Synthetic Gene Coding for hG-CSF in E. coli (Kanamycin Resistance)

The optimized gene Fopt5 was excised from the plasmid pET3a/P-Fopt5 bearing the ampicilline resistance with the restriction enzymes NdeI and BamHI and the gene was then subcloned in the final expression plasmid pET9a bearing the kanamycin resistance (Novagen, Madison USA) which was then transformed in the production strain E. coli BL21 (DE3).

The cultures were prepared on a shaker at 160 rpm for 24-30 h at 25° C.
- in GYSP/kan30 medium (20 g/l phytone, 5 g/l yeast extract, 10 g/l NaCl, 10 g/l glucose, metals in traces, 30 mg/l kanamycin). The induction was performed with the addition of IPTG into the medium to the final concentration of 0.4 mM.
- in GYSP/kan15 medium (20 g/l phytone, 5 g/l yeast extract, 10 g/l NaCl, 10 g/l glucose, metals in traces, 15 mg/l kanamycin). The induction was performed with the addition of IPTG into the medium to the final concentration of 0.4 mM.
- in GYSP medium without the addition of an antibiotic (20 g/l phytone, 5 g/l yeast extract, 10 g/l NaCl, 10 g/l glucose, metals in traces). The induction was performed with the addition of IPTG into the medium to the final concentration of 0.4 mM.

The inoculum was prepared in LBPG/kan30 medium (10 g/l phytone, 5 g/l yeast extract, 10 g/l NaCl, 2.5 g/l glucose) and 30 mg/l kanamycin at 25° C., at 160 rpm overnight.

For SDS-PAGE analysis (the estimation of the content of hG-CSF; expression level) 8 ml of the culture was centrifuged at 5000 rpm. The pellets were then resuspended in 10 mM Tris HCl/pH=8.0 in a proportion of 0.66 ml buffer added to calculated 1 unit $OD_{600nm}$.

The samples were mixed in the proportion of 3:1 with 4×SDS—sample buffer with DTT (pH=8.7) and heated 10 minutes at 95° C., centrifuged and the clear supernatant was loaded on the gel. The content (%) of the accumulated hG-CSF, found in the form of inclusion bodies for the optimized gene are described in Table 2.

TABLE 2

Accumulation level of hG-CSF for the optimized gene (Fopt5) in pET9a vector bearing the kanamycin resistance

| Expression system | cultivation and induction conditions cultivation temperature 25° C. | hG-CSF content (%) in total proteins |
|---|---|---|
| E. coli BL21 (DE3) pET9a-Fopt5 | medium GYSP/kan30 0.4 mM IPTG | >52% |
| E. coli BL21 (DE3) pET9a-Fopt5 | medium GYSP/kan15 0.4 mM IPTG | >53% |
| E. coli BL21 (DE3) pET9a-Fopt5 | medium GYSP 0.4 mM IPTG | >53% |

Figure 5:
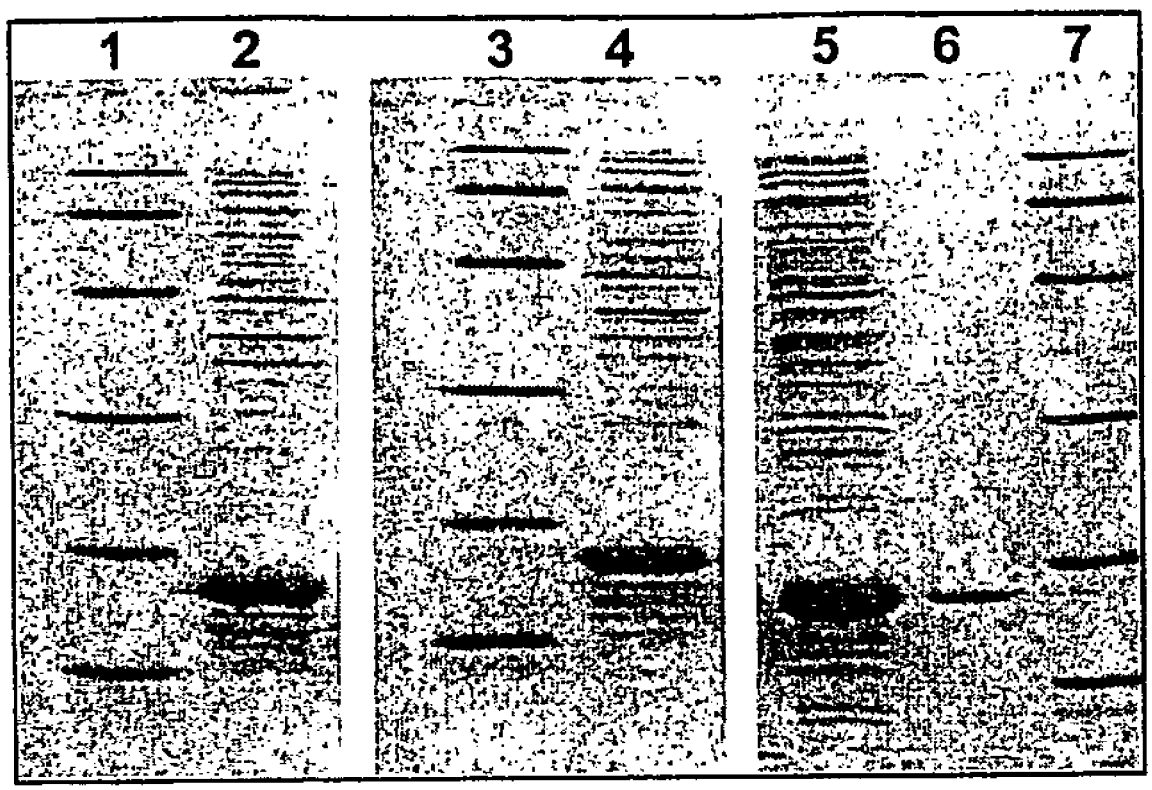
FIG. 5 shows an SDS-PAGE analysis of samples of proteins obtained from the expression of optimized (Fopt5) gene coding for hG-CSF in induced culture of *E. coli* according to an alternative embodiment, as evaluated by dye staining.

FIG. 5 shows the SDS-PAGE (4% stacking, 15% separating; stained with Coomassie brilliant blue) of the samples of the proteins from the induced culture of production strain E. coli BL21 (DE3) with the expression plasmid pET9a-Fopt5 at 25° C. The cultures were cultivated at two different kanamycin concentrations and without kanamycin, specifically in GYSP/kan30, GYSP/kan15 and GYSP medium.

Legend:

Lane 1: LMW (BioRad)

Lane 2: BL21(DE3) pET9a-Fopt5 in GYSP/kan30 medium induced with IPTG at 25° C. (5 µl) (above 52% hG-CSF)

Lane 3: LMW (BioRad)

Lane 4: BL21(DE3) pET9a-Fopt5 in GYSP/kan15 medium induced with IPTG at 25° C. (5 µl) (above 54% hG-CSF)

Lane 5: BL21(DE3) pET9a-Fopt5 in GYSP medium induced with IPTG at 25° C. (5 µl) (above 53% hG-CSF)

Lane 6: hG-CSF standard

Lane 7: LMW (BioRad)

The above cited amounts of the hG-CSF content are obtained with the densitometric analysis of the SDS-PAGE gels stained with Coomassie brilliant blue. The relative amount of hG-CSF for the estimation of expression level was determined with the profile analysis (program Molecular analyst; BioRad) of the gels by using the apparatus Imaging densitometer Model GS670 (BioRad).

The results show that the accumulation of hG-CSF is of the same order (more than 53%) also in the culture without kanamycin, i.e. without the selection pressure. This indicates that the strain is particularly suitable for use on the industrial scale.

The invention claimed is:

1. A synthetic DNA sequence coding for hG-CSF, comprising the nucleotide sequence of SEQ ID NO: 1.

2. A DNA sequence according to claim 1, wherein the sequence provides an expression level of G-CSF, of the total proteins after expression, of at least 50% in an expression system, as quantified by staining protein bands after separation by SDS-PAGE.

3. An expression plasmid, wherein the plasmid comprises a DNA sequence according to claim 1, and a plasmid vector.

4. An expression plasmid according to claim 3, wherein the plasmid vector comprises a T7 promoter sequence.

5. An expression plasmid according to claim 3, wherein the plasmid vector is selected from the group of pET vectors.

6. An expression plasmid according to claim 3, wherein the plasmid vector further comprises a resistance gene selected from the group consisting of an ampicillin resistance gene and a kanamycin resistance gene.

7. An expression system for the expression of a DNA sequence coding for hG-CSF wherein the sequence comprises the nucleotide sequence of SEQ ID NO:1, and wherein the system comprises the expression plasmid according to claim 3 and a production strain of E. coli.

8. An expression system according to claim 7, wherein the production strain is E. coli BL21 (DE3).

9. An expression system according to claim 8, wherein the expression system is substantially free of an antibiotic.

10. A process for the expression of hG-CSF, comprising expressing in E. coli a DNA sequence according to the expression plasmid of claim 3.

11. A process for expression of hG-CSF according to claim 10, wherein IPTG is used for induction at a concentration in the range of about 0.1 mM to about 1 mM.

12. A process according to claim 10, which comprises a fermentation step performed at a temperature of about 20° C. to 30° C.

13. A process according to claim 10, wherein the hG-CSF is in inclusion bodies.

* * * * *

UNITED STATES PATENT AND TRADEMARK OFFICE
CERTIFICATE OF CORRECTION

PATENT NO. : 7,655,437 B2
APPLICATION NO. : 10/522827
DATED : February 2, 2010
INVENTOR(S) : Simona Jevsevar and Viktor Menart It is certified that error appears in the above-identified patent and that said Letters Patent is hereby corrected as shown below:

Column 3, line 21, after "pharmaceutical" and before "Pre-" insert --composition.--

Please delete Column 6, line 48 and replace with "(GGT→GGG) introduction of ApaI (309) restriction site."

Please delete Column 6, line 50 and replace with "*Thr2 (ACC→ACA), Pro3 (CCC→CCA), Gly5*"

Please delete Column 6, line 51 and replace with "*(GGC→GGT), Pro6 (CCT→CCA), Ala7 (GCC→GCT),*"

Please delete Column 6, line 52 and replace with "*Ser8 (AGC→TCT), Ser9 (TCC→TCT),*"

Please delete Column 6, line 53 and replace with "Pro11 (CCC→CCG), *Gln12 (CAG→CAA), Phe14*"

Please delete Column 6, line 54 and replace with "*(TTC→TTT), Leu16 (CTC→TTG),* Lys17 (AAG→AAA),"

Please delete Column 6, line 55 and replace with "*Cys18 (TGC-TGT),* Glu20 (GAG→GAA), *Val22*"

Please delete Column 6, line 56 and replace with "*(GTG→GTT),* Arg23 (AGG→CGT), Lys24 (AAG→AAA),"

Please delete Column 6, line 57 and replace with "*Ile25 (ATC→ATT), Gln26 (CAG→CAA), Gly27*"

Please delete Column 6, line 58 and replace with "*(GGC→GGT), Gly29 (GGC→GGT), Ala31 (GCG-GCT),*"

Signed and Sealed this

Fourteenth Day of December, 2010

David J. Kappos
*Director of the United States Patent and Trademark Office*

CERTIFICATE OF CORRECTION (continued)
U.S. Pat. No. 7,655,437 B2

Please delete Column 6, line 59 and replace with "*Leu32 (CTC→TTA), Gln33 (CAG→CAA),*"

Please delete Column 6, line 60 and replace with "<u>Glu34 (GAG→GAA)</u>, <u>Lys35 (AAG→AAA)</u>, *Ala38*"

Please delete Column 6, line 61 and replace with "*(GCC→GCA), Thr39 (ACC→ACT), Tyr40 (TAC-TAT),*"

Please delete Column 6, line 62 and replace with "<u>*Lys41 (AAG→AAA)*</u>, *Cys43 (TGC→TGT), His44*"

Please delete Column 6, line 63 and replace with "*(CAC-CAT), Pro45 (CCC-CCA),* <u>Glu46 (GAG→GAA)</u>,"

Please delete Column 6, line 64 and replace with "<u>*Glu47 (GAG→GAA)*</u>, *Val49 (GTG→GTT), Leu51*"

Please delete Column 6, line 65 and replace with "*(CTC→TTA),* <u>Gly52 (GGA→GGT)</u>, *His53 (CAC-CAT),*"

Please delete Column 6, line 66 and replace with "*Gly56 (GGC→GGT), Ile57 (ATC→ATT),*"

Please delete Column 6, line 67 and replace with "<u>Pro58 (CCC→CCG)</u>, Pro61 (CCC→CCT),"

Please delete Column 7, line 4 and replace with "*Cys65 (TGC→TGT),* <u>Pro66 (CCC→CCG)</u>,"

Please delete Column 7, line 5 and replace with "<u>Ala69 (GCC→GCG)</u>, <u>Leu76 (TTG-CTG)</u>,"

Please delete Column 7, line 6 and replace with "<u>Leu79 (CTC→CTG)</u>, *Gly82 (GGC→GGT),*"

Please delete Column 7, line 7 and replace with "<u>Leu83 (CTT→CTG)</u>, *Phe84 (TTC→TTT),*"

Please delete Column 7, line 8 and replace with "<u>Leu85 (CTC→CTG)</u>, *Tyr86 (TAC→TAT),*"

Please delete Column 7, line 9 and replace with "*Gly88 (GGG→GGT),* <u>Leu89 (CTC→CTG)</u>,"

Please delete Column 7, line 10 and replace with "Ala92 <u>(GCC→GCG)</u>, <u>Gly95 (GGG→GGC)</u>,"

Please delete Column 7, line 11 and replace with "Ile<u>96 (ATA→ATT)</u>, Pro98 (CCC→CCG),"

Please delete Column 7, line 12 and replace with "<u>*Glu99 (GAG→GAA)*</u>, <u>Leu100 (TTG→CTG)</u>, Gly101"

Please delete Column 7, line 13 and replace with "(GGT→GGG)"

Please delete Column 7, line 18 and replace with "Arg148 (CGG→CGT), Gly150 (GGA→GGT)"

CERTIFICATE OF CORRECTION (continued)
U.S. Pat. No. 7,655,437 B2

Please delete Column 7, line 23 and replace with "*Gln159 (CAG→CAA), Ser160 (AGC→TCT), Phe161*"

Please delete Column 7, line 24 and replace with "*(TTC-TTT),* <u>*Glu163 (GAG→GAA)*</u>*, Val164 (GTG-GTT)*"

Please delete Column 7, line 25 and replace with "<u>Ser165 (TCG→AGC)</u>, *Tyr166 (TAC→TAT), Arg167*"

Please delete Column 7, line 26 and replace with "*(CGC→CGT),* <u>Leu169 (CTA→CTG)</u>, *Arg170*"

Please delete Column 7, line 27 and replace with "*(CGC→CGT), His171 (CAC→CAT),* <u>Leu172 (CTT→CTG)</u>,"

Please delete Column 7, line 28 and replace with "*Ala173 (GCG→GCT),* <u>Pro175 (CCC→CCG)</u>"

<u>In the Claims</u>:

Claim 7, Column 26, line 33, after "sequence of SEQ", delete "TD" and insert --ID--.

SEQUENCE LISTING

<160> NUMBER OF SEQ ID NOS: 26

<210> SEQ ID NO 1
<211> LENGTH: 525
<212> TYPE: DNA
<213> ORGANISM: artificial
<220> FEATURE:
<223> OTHER INFORMATION: synthetic

<400> SEQUENCE: 1

```
atgacaccac tgggtccagc ttcttctctg ccgcaaagct ttctgttgaa atgtttagaa      60
caagttcgta aaattcaagg tgatggtgca gctttacaag aaaaactgtg tgcaacttat     120
aaactgtgtc atccagaaga actggttctg ttaggtcatt ctctgggtat ccgtgggct      180
cctctgagct cctgtccgag ccaggcgctg cagctggcag gctgcctgag ccaactgcat     240
agcggtctgt ttctgtatca gggtctgctg caggcgctgg aaggcatttc cccggaactg     300
gggcccacct tggacacact gcagctggac gtcgccgact tgccaccac catctggcag     360
cagatggaag aactgggaat ggcccctgcc ctgcagccca cccagggtgc catgccggcc     420
ttcgcctctg ctttccagcg ccgtgcaggt ggggtcctgg ttgctagcca tctgcaatct     480
tttctggaag ttagctatcg tgttctgcgt catctggctc agccg                     525
```

<210> SEQ ID NO 2
<211> LENGTH: 528
<212> TYPE: DNA
<213> ORGANISM: artificial
<220> FEATURE:
<223> OTHER INFORMATION: synthetic

<400> SEQUENCE: 2

```
atgacaccac tgggtccagc ttcttctctg ccgcaaagct ttctgttgaa atgtttagaa      60
caagttcgta aaattcaagg tgatggtgca gctttacaag aaaaactgtg tgcaacttat     120
aaactgtgtc atccagaaga actggttctg ttaggtcatt ctctgggtat ccgtgggct      180
cctctgagct cctgtccgag ccaggcgctg cagctggcag gctgcctgag ccaactgcat     240
agcggtctgt ttctgtatca gggtctgctg caggcgctgg aaggcatttc cccggaactg     300
gggcccacct tggacacact gcagctggac gtcgccgact tgccaccac catctggcag     360
cagatggaag aactgggaat ggcccctgcc ctgcagccca cccagggtgc catgccggcc     420
ttcgcctctg ctttccagcg ccgtgcaggt ggggtcctgg ttgctagcca tctgcaatct     480
tttctggaag ttagctatcg tgttctgcgt catctggctc agccgtga                  528
```

<210> SEQ ID NO 3
<211> LENGTH: 525
<212> TYPE: DNA
<213> ORGANISM: Homo sapiens

<400> SEQUENCE: 3

```
atgaccccc tgggccctgc cagctccctg ccccagagct tcctgctcaa gtgcttagag      60
caagtgagga agatccaggg cgatggcgca gcgctccagg agaagctgtg tgccaccac     120
aagctgtgcc accccgagga gctggtgctg ctcggacact ctctgggcat cccctgggct     180
ccctgagct cctgccccag ccaggccctg cagctggcag gctgcttgag ccaactccat     240
agcggccttt tcctctacca ggggctcctg caggccctgg aagggatatc ccccgagttg     300
ggtcccacct tggacacact gcagctggac gtcgccgact tgccaccac catctggcag     360
cagatggaag aactgggaat ggcccctgcc ctgcagccca cccagggtgc catgccggcc     420
ttcgcctctg ctttccagcg ccgggcagga ggggtcctgg ttgctagcca tctgcagagc     480
ttcctggagg tgtcgtaccg cgttctacgc caccttgcgc agccc                     525
```

<210> SEQ ID NO 4
<211> LENGTH: 20
<212> TYPE: DNA

```
<213> ORGANISM: artificial
<220> FEATURE:
<223> OTHER INFORMATION: synthetic

<400> SEQUENCE: 4
cctggaagga atatccccg                                          20

<210> SEQ ID NO 5
<211> LENGTH: 39
<212> TYPE: DNA
<213> ORGANISM: artificial
<220> FEATURE:
<223> OTHER INFORMATION: synthetic

<400> SEQUENCE: 5
tatgacacca ctgggtccag ctccttctct gccgcaaag                    39

<210> SEQ ID NO 6
<211> LENGTH: 30
<212> TYPE: DNA
<213> ORGANISM: Artificial
<220> FEATURE:
<223> OTHER INFORMATION: synthetic

<400> SEQUENCE: 6
gcagagaaga agctggaccc agtggtgtca                              30

<210> SEQ ID NO 7
<211> LENGTH: 41
<212> TYPE: DNA
<213> ORGANISM: artificial
<220> FEATURE:
<223> OTHER INFORMATION: synthetic

<400> SEQUENCE: 7
ctttctgttg aaatgtttag aacaagttcg taaaattcaa g                 41

<210> SEQ ID NO 8
<211> LENGTH: 36
<212> TYPE: DNA
<213> ORGANISM: artificial
<220> FEATURE:
<223> OTHER INFORMATION: synthetic

<400> SEQUENCE: 8
gaacttgttc taaacatttc aacagaaagc tttgcg                       36

<210> SEQ ID NO 9
<211> LENGTH: 33
<212> TYPE: DNA
<213> ORGANISM: artificial
<220> FEATURE:
<223> OTHER INFORMATION: synthetic

<400> SEQUENCE: 9
gtgatggtgc agctttacaa gaaaaactct gtg                          33

<210> SEQ ID NO 10
<211> LENGTH: 39
<212> TYPE: DNA
<213> ORGANISM: artificial
<220> FEATURE:
<223> OTHER INFORMATION: synthetic

<400> SEQUENCE: 10
gtttttcttg taaagctgca ccatcacctt gaattttac                    39
```

```
<210> SEQ ID NO 11
<211> LENGTH: 42
<212> TYPE: DNA
<213> ORGANISM: artificial
<220> FEATURE:
<223> OTHER INFORMATION: synthetic

<400> SEQUENCE: 11
caacttataa actgtgtcat ccagaagaac tggttctgtt ag                        42

<210> SEQ ID NO 12
<211> LENGTH: 38
<212> TYPE: DNA
<213> ORGANISM: artificial
<220> FEATURE:
<223> OTHER INFORMATION: synthetic

<400> SEQUENCE: 12
cagttcttct ggatgacaca gtttataagt tgcacaca                             38

<210> SEQ ID NO 13
<211> LENGTH: 36
<212> TYPE: DNA
<213> ORGANISM: artificial
<220> FEATURE:
<223> OTHER INFORMATION: synthetic

<400> SEQUENCE: 13
gtcattctct gggtattccg tgggctcctc tgagct                               36

<210> SEQ ID NO 14
<211> LENGTH: 42
<212> TYPE: DNA
<213> ORGANISM: artificial
<220> FEATURE:
<223> OTHER INFORMATION: synthetic

<400> SEQUENCE: 14
cagaggagcc cacggaatac ccagagaatg acctaacaga ac                        42

<210> SEQ ID NO 15
<211> LENGTH: 38
<212> TYPE: DNA
<213> ORGANISM: artificial
<220> FEATURE:
<223> OTHER INFORMATION: synthetic

<400> SEQUENCE: 15
ctctgctttc cagcgccgtg caggtggggt cctggttg                             38

<210> SEQ ID NO 16
<211> LENGTH: 31
<212> TYPE: DNA
<213> ORGANISM: artificial
<220> FEATURE:
<223> OTHER INFORMATION: synthetic

<400> SEQUENCE: 16
ctagccatct gcaatccttt ctggaagtta g                                    31

<210> SEQ ID NO 17
<211> LENGTH: 34
<212> TYPE: DNA
<213> ORGANISM: artificial
<220> FEATURE:
```

<223> OTHER INFORMATION: synthetic

<400> SEQUENCE: 17
acgatagcta acttccagaa aagattgcag atgg           34

<210> SEQ ID NO 18
<211> LENGTH: 38
<212> TYPE: DNA
<213> ORGANISM: artificial
<220> FEATURE:
<223> OTHER INFORMATION: synthetic

<400> SEQUENCE: 18
ctatcgtgtt ctgcgtcatc tggctcagcc gtgataag           38

<210> SEQ ID NO 19
<211> LENGTH: 35
<212> TYPE: DNA
<213> ORGANISM: artificial
<220> FEATURE:
<223> OTHER INFORMATION: synthetic

<400> SEQUENCE: 19
gatccttatc acggctgagc cagatgacgc agaac           35

<210> SEQ ID NO 20
<211> LENGTH: 44
<212> TYPE: DNA
<213> ORGANISM: artificial
<220> FEATURE:
<223> OTHER INFORMATION: synthetic

<400> SEQUENCE: 20
gccctggagg ggatttcccc cgagttgggg cccaccttgg acac           44

<210> SEQ ID NO 21
<211> LENGTH: 40
<212> TYPE: DNA
<213> ORGANISM: artificial
<220> FEATURE:
<223> OTHER INFORMATION: synthetic

<400> SEQUENCE: 21
cctgtccgag ccaggcgctg cagctggcag gctgcctgag           40

<210> SEQ ID NO 22
<211> LENGTH: 35
<212> TYPE: DNA
<213> ORGANISM: artificial
<220> FEATURE:
<223> OTHER INFORMATION: synthetic

<400> SEQUENCE: 22
cctgccagct gcagcgcctg gctcggacag gagct           35

<210> SEQ ID NO 23
<211> LENGTH: 40
<212> TYPE: DNA
<213> ORGANISM: artificial
<220> FEATURE:
<223> OTHER INFORMATION: synthetic

<400> SEQUENCE: 23
ccaactgcat agcggtctgt ttctgtatca gggtctgctg           40

```
<210> SEQ ID NO 24
<211> LENGTH: 40
<212> TYPE: DNA
<213> ORGANISM: artificial
<220> FEATURE:
<223> OTHER INFORMATION: synthetic

<400> SEQUENCE: 24
ctgatacaga aacagaccgc tatgcagttg gctcaggcag                              40

<210> SEQ ID NO 25
<211> LENGTH: 35
<212> TYPE: DNA
<213> ORGANISM: artificial
<220> FEATURE:
<223> OTHER INFORMATION: synthetic

<400> SEQUENCE: 25
caggcgctgg aaggcatttc cccggaactg gggcc                                   35

<210> SEQ ID NO 26
<211> LENGTH: 40
<212> TYPE: DNA
<213> ORGANISM: artificial
<220> FEATURE:
<223> OTHER INFORMATION: synthetic

<400> SEQUENCE: 26
ccagttccgg ggaaatgcct tccagcgcct gcagcagacc                              40
```